(12) United States Patent
Gharehbeglou et al.

(10) Patent No.: US 9,551,715 B1
(45) Date of Patent: Jan. 24, 2017

(54) DEVICE AND METHODS FOR DETECTING CEREBROSPINAL FLUID LEAKAGE

(71) Applicants: Mohammad Gharehbeglou, Tehran (IR); Ali Movahed, Tehran (IR)

(72) Inventors: Mohammad Gharehbeglou, Tehran (IR); Ali Movahed, Tehran (IR)

(*) Notice: Subject to any disclaimer, the term of this patent is extended or adjusted under 35 U.S.C. 154(b) by 0 days.

(21) Appl. No.: 15/076,343

(22) Filed: Mar. 21, 2016

(51) Int. Cl.
  *G01N 33/66* (2006.01)
  *G01N 33/487* (2006.01)
  *G01N 33/68* (2006.01)
  *G01N 33/84* (2006.01)

(52) U.S. Cl.
  CPC ........ *G01N 33/66* (2013.01); *G01N 33/48707* (2013.01); *G01N 33/48721* (2013.01); *G01N 33/48792* (2013.01); *G01N 33/6896* (2013.01); *G01N 33/84* (2013.01); *G01N 2333/79* (2013.01); *G01N 2800/28* (2013.01); *Y10T 436/144444* (2015.01); *Y10T 436/193333* (2015.01)

(58) Field of Classification Search
  CPC G01N 33/48; G01N 33/487; G01N 33/48707; G01N 33/48785; G01N 33/48792; G01N 33/66; G01N 33/68; G01N 21/77; Y10T 436/144444; Y10T 436/19; Y10T 436/193333
  USPC ....... 436/63, 86, 87, 95, 124, 125, 149, 150, 436/164, 169; 422/400, 401, 402, 403, 422/404, 420, 68.1, 82.01; 435/14, 29
  See application file for complete search history.

(56) References Cited

U.S. PATENT DOCUMENTS

| | | | |
|---|---|---|---|
| 6,318,970 B1 | 11/2001 | Backhouse | |
| 6,450,203 B1 | 9/2002 | Backhouse | |
| 7,695,253 B2 | 4/2010 | Yang | |
| 2004/0002168 A1* | 1/2004 | Remington | ............ C07K 16/18 436/518 |
| 2005/0169777 A1 | 8/2005 | Shen | |
| 2006/0062734 A1* | 3/2006 | Melker | ................. A61J 7/0409 424/10.1 |
| 2007/0248497 A1 | 10/2007 | Robillot | |
| 2012/0070314 A1 | 3/2012 | Meuller | |
| 2012/0288959 A1* | 11/2012 | Palmer | ............. G01N 33/54366 436/501 |
| 2013/0287613 A1 | 10/2013 | Gould | |

OTHER PUBLICATIONS

Mantur et al. Clinica Chimica Acta, vol. 412, Feb. 17, 2011, pp. 837-840.*
Chan et al. Asian Journal of Surgery, vol. 27 (1), 2004, pp. 39-42.*

* cited by examiner

*Primary Examiner* — Maureen Wallenhorst
(74) *Attorney, Agent, or Firm* — Falati Law Firm

(57) ABSTRACT

A device for rapid detection of cerebrospinal fluid in a sample fluid, the device uses a sample pad with sensors for detecting the presence of one or more analytes in the sample fluid and an analyzer operatively connected to the sample pad, for quantitative analysis of one or more analytes. A display unit operably connected to the analyzer, for displaying an output of the analysis may also be a part of the device, wherein the display unit may be able to indicate presence or absence of cerebrospinal fluid leakage using an indicator.

20 Claims, 3 Drawing Sheets providing a portable hand-held device for detecting CSF in the sample, wherein the device comprises a sample pad operatively connected to an analyzer, a display unit and an indicator, wherein the analyzer comprises sensors capable of detecting glucose and chloride in the sample (310);

⬇ taking a sample secretion from an ear or nose (320);

⬇ placing on the sample pad of the device, a predefined quantity of the sample secretion taken from the ear or nose (330);

⬇ observing a readily discernible change in the indicator unit, indicating the presence or absence of glucose and chloride (340); and

⬇ reading an output from the display unit of the device, wherein the output is obtained under one minutes from placing the sample secretion on the sample pad of the device, and wherein the presence of both glucose and chloride are indicative of the presence of cerebrospinal fluid in the sample (350).

FIG. 3

DEVICE AND METHODS FOR DETECTING CEREBROSPINAL FLUID LEAKAGE

BACKGROUND OF THE INVENTION

Skull base fracture is one of the most complex medical issues, especially in neurological emergencies and trauma services. Skull fractures occur commonly in patients who are in heavy accidents or severe trauma resulting in a critical health condition. Cerebrospinal fluid (CSF) leakage is a problem that is frequently associated with base skull fractures. CSF leakage can occur anywhere along the craniospinal axis and the most common clinical manifestation of CSF leakage involves rhinorrhea and/or otorrhea.

Cerebrospinal fluid (CSF) leakage can also occur under non-traumatic conditions such as leaks caused directly or indirectly by tumors, hydrocephalus, osteomyelitic erosion and congenital abnormalities. Clinical manifestations of CSF leakage range from drainage of CSF that is easily recognized to slow, intermittent leakage that can be difficult to diagnose. Cerebrospinal fluid leakage may be traumatic, iatrogenic, or spontaneous in origin, and it affects a relatively large proportion of neurosurgical patients.

Cerebrospinal fluid (CSF) leakage is generally detected based on analysis of samples such as nasal discharge or secretions from ear or nose of a patient. The samples collected from patients will be sent from a sampling location to a laboratory for analysis, which is a time consuming process, for example, the analysis may take many hours or even a few days. The time delay may lead to further deterioration of patient's condition and prolongs the time required for making critical decisions. Further, the report of the analysis would require a medical technician to collect and process clinical samples and a qualified medical professional to interpret the results.

In traditional methods of CSF detection, sample fluids from the patient's nose or ear are collected inside a sample tube and sent to laboratories to accurately determine the quantities of analytes such as glucose, chloride and beta-2 transferrin. The above method consumes a considerable amount of time for transporting the sample to the laboratory and analyzing the sample at the laboratory. The above method also provides results in a format which can be clearly interpreted only by a qualified medical professional, which might further delay the time to take critical clinical decisions, such as opting for surgery. Due to the typically urgent nature of this medical problem, any delay in diagnosing CSF leakage can increase the risk of mortality.

Therefore, there is a need in the art for a device and a method for rapid detection of cerebrospinal fluid leakage, thereby helping in making faster decisions regarding emergency medical treatments and reducing mortality rate among head trauma patients. In addition, there is a need in the art for a device that can easily handle and rapidly provide a readily discernible output of the analysis for determining CSF leakage.

SUMMARY OF THE INVENTION

The present invention generally relates to cerebrospinal fluid leakage detection and more specifically relates to a device and a method for rapid detection of cerebrospinal fluid in a fluid sample comprising secretions collected from the nose or ear of a patient.

One aspect of the present disclosure is a hand held portable device for detecting cerebrospinal fluid in a fluid sample, the device comprising a sample pad comprising sensors for detecting the presence of at least one analyte in the sample fluid; an analyzer operatively connected to the sample pad, for quantitative analysis of the analyte; and a display unit operably connected to the analyzer, for displaying an output of the analysis, wherein the display unit further comprises an indicator for indicating presence or absence of cerebrospinal fluid leakage.

In one embodiment the device further comprises a serial communication interface for connecting to a computing device. In another embodiment, the analyte is selected from a group consisting of glucose, chloride, beta-transferrin, and any combination thereof. In one embodiment, the analyte is chloride or glucose, or both chloride and glucose. That is, the device is capable of measuring, in one example, glucose or chloride levels as well as concurrently measuring for both chloride and glucose levels in the sample. In one embodiment, the device is no larger than 30 cm length, 15 cm width and 7 cm height, and wherein the indicator comprises a red light for indicating cerebrospinal fluid leakage and a green light for indicating no cerebrospinal fluid leakage.

In one embodiment, the sample pad further comprises a sample port for receiving the sample fluid. In another embodiment, the sensor comprises a chemical sensor or an electrical sensor or both. In one embodiment, the analyzer further displays a standard range of the analyte concentration for adults and children.

One aspect of the present disclosure is a method for detection of cerebrospinal fluid leakage, the method comprising: i) providing a device for detecting CSF leakage, wherein the device comprises a sample pad operatively connected to an analyzer and a display unit; ii) placing in the sample pad of the device, a predefined quantity of a sample secretion collected from the ear or the nose, wherein the analyzer is capable of detecting the presence and concentration of one or more analytes in the sample; iii) observing a readily discernible change in an indicator of the display unit, indicating presence or absence of cerebrospinal fluid leakage, based on presence or absence of one or more analytes; and iv) reading an output from the display unit of the device.

In one embodiment, the device is a portable, hand-held device and the indicator comprises a red light for indicating cerebrospinal fluid leakage and a green light for indicating no cerebrospinal fluid leakage. In one embodiment, the sample pad further comprises a sample port for receiving the sample fluid. In one embodiment, the sensor is selected from a group consisting of a chemical sensor and an electrical sensor. In another embodiment, the display unit further displays a standard range of the analyte concentration for adults and children.

Another aspect of the present disclosure is a method for the rapid detection of cerebrospinal fluid (CSF) in a sample, comprising: i) providing a device for detecting CSF in the sample, wherein the device is a portable hand-held device comprising a sample pad operatively connected to an analyzer, a display unit and an indicator, wherein the analyzer comprises one or more sensors capable of detecting one or more analytes in the sample; ii) placing in the sample pad of the device, a predefined quantity of a sample comprising ear or nasal secretion; iii) observing a readily discernible change in the indicator unit, indicating the presence or absence of one or more analytes; and iv) reading an output from the display unit of the device, wherein the output displays the concentration of one or more analytes present in the sample. In one embodiment, the one or more analytes are selected from a group consisting of glucose, chloride and beta-transferrin. In one embodiment, the one or more analytes is selected from a group consisting of glucose and chloride.

Another aspect of the present disclosure is a method for the rapid detection of cerebrospinal fluid (CSF) in a sample, comprising: i) providing a device for detecting CSF in the sample, wherein the device is a portable hand-held device comprising a sample pad operatively connected to an analyzer, a display unit and an indicator, wherein the analyzer comprises one or more sensors capable of detecting chloride and/or glucose in the sample; ii) placing in the sample pad of the device, a predefined quantity of a sample comprising ear or nasal secretion; iii) observing a readily discernible change in the indicator unit, indicating the presence or absence of chloride and/or glucose; and iv) reading an output from the display unit of the device, wherein the output displays the concentration of chloride and/or glucose present in the sample.

In one embodiment, the indicator comprises a red light for indicating cerebrospinal fluid leakage and a green light for indicating no cerebrospinal fluid leakage. In another embodiment, the sample pad further comprises a sample port for receiving the sample fluid. In one embodiment, the one or more sensors are selected from a group consisting of a chemical sensor and an electrical sensor.

One aspect of the present disclosure is directed to a portable hand-held device for detecting cerebrospinal fluid in a fluid sample from the ear or nose of a patient, comprising: a sample pad comprising one or more sensors capable of detecting at least one analyte in a fluid sample taken from the ear or nose of a patient, wherein the at least one analyte is selected from a group consisting of glucose, chloride, and beta-transferrin; an analyzer operatively connected to the sample pad, wherein the analyzer quantitative analyses the presence or absence of the one or more analytes from the group consisting of glucose, chloride, and beta-transferrin; and a display unit operably connected to the analyzer, for displaying an output of the analysis, wherein the display unit further comprises an indicator for indicating the presence or the absence of cerebrospinal fluid in a fluid sample.

Another aspect of the present disclosure is directed to a method for rapidly detecting cerebrospinal fluid leakage in a patient, comprising: i) providing a portable hand-held device for detecting the presence or absence of CSF in a fluid sample from the patient, wherein the portable hand-held device comprises a sample pad operatively connected to an analyzer and a display unit; ii) collecting a sample of a secretion from the nose or the ear of the patient; iii) placing on the sample pad of the device, a predefined quantity of the sample, wherein the analyzer is capable of detecting the presence and concentration in the sample of one or more analytes selected from a group consisting of glucose, chloride, and beta-transferrin; iv) detecting the presence or absence of the one or more analytes in under three minutes; and v) observing a readily discernible change in an indicator on the display unit, the result of which indicates the presence or absence of cerebrospinal fluid in the sample and by extension provides for the rapid detection of cerebrospinal fluid leakage in a patient.

In one embodiment, CSF leakage is detected if the glucose level in the sample is between 40-80 mg/dl and the chloride level in the sample is between 116-128 mmol/L. In one embodiment, if the glucose level in the sample is 40 mg/dl or above and the chloride level in the sample is 116 mmol/L or above, CSF leakage is detected.

One aspect of the present disclosure is directed to a method for rapidly detecting cerebrospinal fluid (CSF) in a sample, said method comprising: i) providing a portable hand-held device for detecting CSF in the sample, wherein the device comprises a sample pad operatively connected to an analyzer, a display unit and an indicator, wherein the analyzer comprises sensors capable of detecting glucose and chloride in the sample; ii) taking a sample secretion from an ear or nose; iii) placing on the sample pad of the device, a predefined quantity of the sample secretion taken from the ear or nose; iv) observing a readily discernible change in the indicator unit, indicating the presence or absence of glucose and chloride; and v) reading an output from the display unit of the device, wherein the output is obtained under one minute from placing the sample secretion on the sample pad of the device, and wherein the presence of both glucose and chloride are indicative of the presence of cerebrospinal fluid in the sample. In one example, the display unit displays the concentration of the glucose and chloride present in the sample. In one embodiment, CSF leakage is detected if the glucose level in the sample is between 40-80 mg/dl and the chloride level in the sample is between 116-128 mmol/L.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

FIG. 3 illustrates a flow diagram showing a method for detection of CSF leakage using glucose and chloride as markers.

DETAILED DESCRIPTION OF EMBODIMENTS

Figure 1:
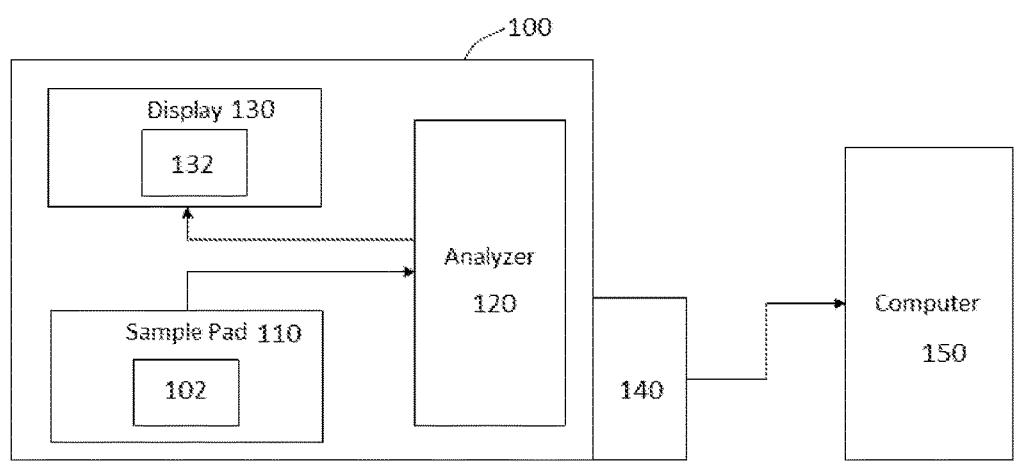
FIG. 1 illustrates a block diagram showing different components of the device for detecting CSF leakage.

Skull base fracture is one of the most complex medical issues, especially in neurological emergencies and trauma services. Skull fracture occurs commonly in patients who are in heavy accidents or severe trauma resulting in a critical health condition. Cerebrospinal fluid (CSF) leakage is a problem that is frequently associated with base skull fractures, therefore rapid and timely diagnosis of CSF leakage enables the care provider to make rapid clinical decisions, such as carrying out an emergency surgery, and can significantly reduce mortality in patients with head trauma. CSF leakage can occur anywhere along the craniospinal axis and the most common clinical manifestation of CSF leakage involves rhinorrhea and/or otorrhea.

The presently disclosed device comprises a housing with a sample pad comprising sensors for detecting the presence of one or more analytes in the sample fluid. The sample pad is operatively connected to an analyzer for quantitative analysis of one or more analytes. The device further comprises a display unit operably connected to the analyzer for displaying an output of the analysis. The display unit further comprises an indicator for immediately indicating presence or absence of cerebrospinal fluid leakage.

In an embodiment, the device for detection of cerebrospinal fluid leakage comprises at least one sensor capable of analyzing the presence and concentration of at least one analyte selected from a group consisting of glucose and chloride. In another embodiment, the device comprises a plurality of sensors capable of analyzing the concentration of multiple analytes comprising glucose, chloride and beta-2 transferrin. In one example, the analyte is chloride. In one example, the analyte is glucose. In another example, the analyte is glucose and/or chloride. Alternatively, the analyte can be beta-2 transferrin. In another example, the sample is tested for glucose, chloride and beta-2 transferrin.

The indicator comprises a red LED light configured to illuminate to indicate the CSF leakage and a green LED light configured to illuminate when there is no CSF leakage, thereby providing a readily discernible output. The display unit is configured to display the concentration level of one or more analytes present in the test sample. In another embodiment, the display unit further shows a comparison between the concentrations of analytes present in the test sample against the standard concentration of analytes normally present in the same sample from children and adults, which forms the basis of determining CSF leakage.

The present invention also relates to a method for rapid detection of cerebrospinal fluid leakage, the method comprises the following steps of: i) providing a device for detection of CSF leakage, wherein the device comprises a sample pad operatively connected to an analyzer and a display unit; ii) placing in the sample pad of the device, a predefined quantity of a sample secretion collected from ear or nose, wherein the analyzer is capable of detecting the presence and concentration of one or more analytes in the sample; iii) observing a readily discernible change in an indicator of the display unit, indicating presence or absence of cerebrospinal fluid leakage, based on presence or absence of one or more analytes; and iv) reading an output from the display unit of the device.

In an embodiment, the present invention relates to a method for rapid detection of cerebrospinal fluid (CSF) in a sample. The method comprises the following steps of: i) providing a device for detection of CSF in a sample, wherein the device comprises a sample pad operatively connected to an analyzer, a display unit and an indicator, wherein the analyzer comprises one or more sensors capable of detecting one or more analytes in the sample; ii) placing in the sample pad of the device, a predefined quantity of a sample comprising ear or nasal secretion; iii) observing a readily discernible change in the indicator unit, indicating the presence or absence of one or more analytes; and iv) reading an output from the display unit of the device, wherein the output displays the concentration of one or more analytes present in the sample.

A description of embodiments of the present invention will now be given with reference to the Figures. It is expected that the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The present invention discloses a device for rapid detection of cerebrospinal fluid (CSF) leakage by detecting and quantifying the presence of cerebrospinal fluid in a sample secretion obtained from nose or ear of patients. CSF leakage is determined by the analyzing the concentration level of one or more analytes (typically present in CSF) in the fluid sample from the ear or the nose of individuals.

Referring to FIG. 1, illustrating a block diagram of the device 100 for detecting CSF leakage, comprises a sample pad 110 comprising sensors 102 for detecting the presence of one or more analytes in the sample fluid. The sample pad 110 is operatively connected to an analyzer 120 for quantitative analysis of the analytes. The device 100 further comprises a display unit 130 operably connected to the analyzer 120 for displaying an output of the analysis. The display unit 130 further comprises an indicator 132 for immediately indicating presence or absence of cerebrospinal fluid leakage. A serial communication interface 140, for example RS232, for connecting the device 100 to a computing device 150 such as a computer.

The analytes comprise one or more of the compounds selected from a group consisting glucose, chloride, transferrin, beta-1 transferrin and beta-2 transferrin. In an embodiment, the concentration of one or more analytes present in the test sample is compared against the standard concentration of analytes normally present in same sample from children and adults. This comparison to normal levels in healthy individuals forms the basis of determining CSF leakage. The display unit 130 provides the concentration level of analytes in the test sample and also displays normal ranges of the analytes in adults and children.

In an embodiment, the indicator 132 comprises a red LED light 134 configured to illuminate or glow to indicate CSF leakage and a green LED light 136 is configured to illuminate when there is no CSF leakage, thereby providing a readily discernible output. The indicator 132 provides an advantage of receiving immediate output which can be easily interpreted by a medical technician and does not require interpretation by a physician each time. Rapid detection of CSF leakage helps in making critical clinical decisions such as carrying out emergency surgery and ultimately reduces mortality rate associated with head trauma.

Generally, CSF leakage is detected based on the analysis of nasal discharges by sending the nasal discharge sample to a laboratory, which consumes lots of time ranging from several hours to days. Whereas, the device of the present invention uses chemical sensors to measure the concentration of glucose and chloride in the sample obtained from ear or nose secretions, in order to detect CSF leakage in skull base fractures. The present device requires only few drops of sample (for example, 2-5 ml) from the patient to diagnose CSF leak within seconds. In one embodiment, the sample required can be less than 1 ml, for example, 300 micro liters.

The time taken for the presently disclosed device to provide an output that enables a diagnosis of CSF leakage to be made can be up to 30 seconds, 60 seconds, 120 seconds, 180 seconds, or up to 300 seconds. In one example, the result is provided within one minute. The device comprises a handheld device which can be used by the bedside, facilitating collection and rapid analysis of the sample. This is extremely relevant and beneficial in emergency settings, especially where patients are brought to the Emergency Room of hospitals after head trauma and time is of the essence.

To Applicants' knowledge no such handheld device or similar device exists which can rapidly be used to detect CSF leakage. Applicants have discovered a device that can remedy this deficiency in the art. The inventors of the present disclosure have discovered that by measuring the amounts of glucose, chloride transferrin, beta-1 transferrin, beta-2 transferrin, and combinations thereof from samples taken from the nose or ears of patients, it is possible to detect CSF leakage. In one embodiment, the presently disclosed device measures glucose or chloride, or both glucose and chloride. The device and method of the present invention allows for the rapid identification of patients who have CSF leakage and can be of immense value to physicians in an emergency setting.

The analyzer can be preprogrammed with normal threshold ranges for one or more analytes and if the analyte concentration in the sample exceeds the threshold, the red light will illuminate indicating a "CSF leakage". Similarly, if the analyte concentration in the sample falls below the threshold, the green light will illuminate indicating that there is "no CSF leakage".

Figure 2:
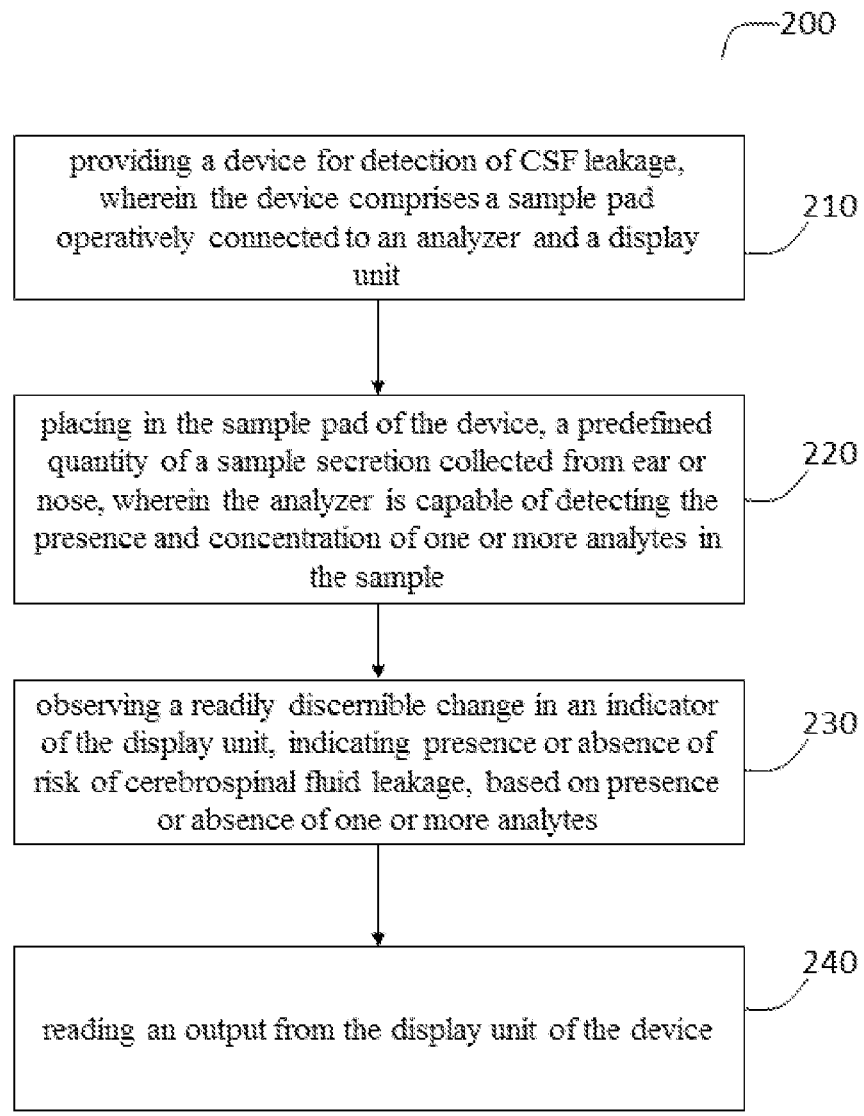
FIG. 2 illustrates a flow diagram showing a method for detection of CSF leakage.

Referring to FIG. 2, illustrating a method for rapid detection of cerebrospinal fluid leakage comprises the following steps of: i) providing a device for detection of CSF leakage, wherein the device comprises a sample pad operatively connected to an analyzer and a display unit, as shown in step 210; ii) placing in the sample pad of the device, a predefined quantity of a sample secretion collected from ear or nose, wherein the analyzer is capable of detecting the presence and concentration of one or more analytes in the sample, as shown in step 220; iii) observing a readily discernible change in an indicator of the display unit, indicating presence or absence of cerebrospinal fluid leakage, based on presence or absence of one or more analytes, as shown in step 230; and iv) reading an output from the display unit of the device, as shown in step 240. Based on the change in the indicator, CSF leakage can be determined.

Referring to FIG. 3, illustrating a method for rapidly detecting cerebrospinal fluid (CSF) in a sample, said method comprising: i) providing a portable hand-held device for detecting CSF in the sample, wherein the device comprises a sample pad operatively connected to an analyzer, a display unit and an indicator, wherein the analyzer comprises sensors capable of detecting glucose and chloride in the sample, as shown in step 310; ii) taking a sample secretion from an ear or nose, as shown in step 320; iii) placing on the sample pad of the device, a predefined quantity of the sample secretion taken from the ear or nose, as shown in step 330; iv) observing a readily discernible change in the indicator unit, indicating the presence or absence of glucose and chloride, as shown in step 340; and v) reading an output from the display unit of the device, wherein the output is obtained under one minutes from placing the sample secretion on the sample pad of the device, and wherein the presence of both glucose and chloride are indicative of the presence of cerebrospinal fluid in the sample, as shown in step 350.

In an embodiment, the display unit further displays standard analyte concentration in ear or nose secretions from children and adult. In another embodiment, the display unit also shows a comparison of analyte concentration present in the test sample against known to be present in the same sample from control population.

In one example, the present invention relates to a method for rapid detection of cerebrospinal fluid (CSF) in a sample. The method comprises the following steps of: i) providing a device for detection of CSF in the sample, wherein the device comprises a sample pad operatively connected to an analyzer, a display unit and an indicator, wherein the analyzer comprises one or more sensors capable of detecting one or more analytes in the sample; ii) placing in the sample pad of the device, a predefined quantity of a sample comprising ear or nasal secretion; iii) observing a readily discernible change in the indicator unit, indicating the presence or absence of one or more analytes; and iv) reading an output from the display unit of the device, wherein the output displays the concentration of one or more analytes present in the sample.

One aspect of the present disclosure is directed to a method for rapidly detecting cerebrospinal fluid (CSF) in a sample. The method comprises providing a portable hand-held device for detecting CSF in the sample, wherein the device comprises a sample pad operatively connected to an analyzer, a display unit and an indicator, wherein the analyzer comprises sensors capable of detecting glucose and chloride in the sample. The method further comprises taking a sample secretion from an ear or nose; and placing on the sample pad of the device, a predefined quantity of the sample secretion taken from the ear or nose. The method further comprises observing a readily discernible change in the indicator unit, indicating the presence or absence of glucose and chloride. Moreover, the method further comprises reading an output from the display unit of the device, wherein the output is obtained under one minute from placing the sample secretion on the sample pad of the device, such that the presence of both glucose and chloride are indicative of the presence of cerebrospinal fluid in the sample.

In one example, the display unit displays the concentration of the glucose and chloride present in the sample. CSF leakage is detected, in one example, if the glucose level in the sample is between 40-80 mg/dl and the chloride level in the sample is between 116-128 mmol/L. In one example, if the glucose level in the sample is 40 mg/dl or above and the chloride level in the sample is 116 mmol/L or above, CSF leakage is detected.

The analytes comprises one or more of the compounds selected from a group consisting glucose, chloride, transferrin, beta-1 transferrin and beta-2 transferrin. In one example, the analytes comprised glucose and/or chloride. In an embodiment, the concentration of one or more analytes present in the test sample is compared against the standard concentration of analytes normally present in same sample from children and adults, as found in published medical literature. Normal concentration value of glucose and chloride in children and adults' CSF Fluid is known in the art, for example, as provided in text books including on clinical neurology and clinical pathology. The device compares values of samples with values that are existent in individuals who have not been exposed to head trauma or any such injury and are considered as otherwise having normal CSF as known from textbooks on clinical neurology.

The indicator may comprise a red LED light configured to illuminate or glow to indicate CSF leakage and a green LED light configured to illuminate when there is no CSF leakage, thereby providing a readily discernible output. The indicator provides an advantage of receiving immediate output which can be easily interpreted by a medical technician and does not require interpretation by a physician each time. Rapid detection of CSF leakage helps in making critical clinical decisions such as carrying out emergency surgery and ultimately reduces mortality rate associated with head trauma.

The device of the present invention needs only a few drops of sample secretion obtained from ears or nose of the patient suspected of CSF leakage. The device is capable of diagnosing within seconds whether there is CSF leakage or not. The device plays a major role in diagnosis of CSF leakage, especially leakage in patients with skull base fractures. The device can play a major role in determining CSF leakage in skull base fracture patients by measuring the level of glucose and chloride in the cerebrospinal fluid secreted in droplets from the patient's ear or nose. The device displays the standard level of glucose and chloride in a similar sample from children and adults.

The device of the present invention takes less time for analysis and costs significantly less than the currently used laboratory methods. Rapid detection of CSF leakage facilitates in making swift decisions concerning the patient, thus reducing the fatality, especially in trauma cases. The device will be immensely beneficial since the device can provide a quick emergency diagnosis of cerebrospinal fluid leak that can help the patient to receive vital medical treatments faster. The disclosed device for detection of CSF leakage can be used in emergency centers, clinics and neurosurgery wards in hospitals.

The devices and methods of the invention provide a safe, efficient, and a rapid mode of detecting CSF leakage with high specificity and sensitivity. For example, the devices and methods of the invention may be used along patient bed side, immediately after a trauma or a head injury to test for CSF leakage in a patient. They may also be used during-surgery or post-surgery, especially in head and brain surgery, or to test samples obtained during and after neural blockade.

The devices and methods of the invention are utilized in a variety of clinical settings to determine the presence of CSF in a sample, including skull fractures. CSF leaks following various surgeries, such as endoscopic endonasal surgery, neurosurgery, epidural catheter placement, spontaneous intracranial hypotension, anthrax induced intracranial hypotension, or CSF leaks associated conditions such as rhinorhea and otorrhea, hydrocephalus, intracranial neoplasms, congenital neural malformations, and the like.

One aspect of the present disclosure is a device for detecting cerebrospinal fluid in a fluid sample. The device can a hand-held portable device comprising a sample pad that includes sensors for detecting the presence of at least one analyte in the sample fluid. The device further comprises an analyzer operatively connected to the sample pad, for quantitative analysis of the analyte; and a display unit operably connected to the analyzer, for displaying an output of the analysis. The display unit comprises an indicator for indicating presence or absence of cerebrospinal fluid leakage. The device further comprises a serial communication interface for connecting to a computing device. The analyte is selected from a group consisting of glucose, chloride, beta-transferrin, and any combination thereof. The size of the device may be any size that can be held by an average build user in one hand. It is portable and in one example is no larger than 30 cm length, 15 cm width and 7 cm height. The device may further comprise an indicator with a red light for indicating cerebrospinal fluid leakage and a green light for indicating no cerebrospinal fluid leakage.

The sample pad further comprises a sample port for receiving the sample fluid. The sensor may comprise a chemical sensor or an electrical sensor or both a chemical and an electrical sensor. The analyzer may further display a standard range of the analyte concentration for adults and children who have not had any head trauma. This standard range can be used as an immediate reference point for the sample being analyzed.

The present disclosure is also directed to a method for detection of cerebrospinal fluid leakage. The method comprises providing a device for detecting CSF leakage, wherein the device comprises a sample pad operatively connected to an analyzer and a display unit. The method further comprises placing in the sample pad of the device, a predefined quantity of a sample secretion collected from the ear or the nose, wherein the analyzer is capable of detecting the presence and concentration of one or more analytes in the sample. Furthermore, the method comprises observing a readily discernible change in an indicator of the display unit, indicating presence or absence of cerebrospinal fluid leakage, based on presence or absence of one or more analytes; and reading an output from the display unit of the device.

The device is a portable, hand-held device and the indicator comprises a red light for indicating cerebrospinal fluid leakage and a green light for indicating no cerebrospinal fluid leakage. The sample pad further comprises a sample port for receiving the sample fluid. The sensor is selected from a group consisting of a chemical sensor and an electrical sensor. The display unit further displays a standard range of the analyte concentration for adults and children.

Another aspect of the present disclosure is a method for the rapid detection of cerebrospinal fluid (CSF) in a sample. The method comprises providing a device for detecting CSF in the sample, wherein the device is a portable hand-held device comprising a sample pad operatively connected to an analyzer, a display unit and an indicator, wherein the analyzer comprises one or more sensors capable of detecting one or more analytes in the sample. The method further comprises placing in the sample pad of the device, a predefined quantity of a sample comprising ear or nasal secretion; and observing a readily discernible change in the indicator unit, indicating the presence or absence of one or more analytes.

Moreover, the method of the present invention comprises reading an output from the display unit of the device wherein the output displays the concentration of one or more analytes present in the sample. The one or more analytes can be glucose, chloride and/or beta-transferrin. In one example, the indicator comprises a red light for indicating cerebrospinal fluid leakage and a green light for indicating no cerebrospinal fluid leakage. The one or more sensors can be a chemical sensor, an electrical sensor, and/or both an electrical and a chemical sensor.

Nasal fluid has very little glucose (generally <10 mg/ml in fluids) and normal CSF glucose level is 40-80 mg/dl. Similarly, nasal fluid chloride levels approximate that of serum, yet, CSF chloride levels are significantly higher, in the range of 116-128 mmol/L. In one example, 20 patients with symptoms of Skull Base fracture were randomly selected. Nine were male and 6 were female. Their average age was about 42 years old. When admitted to the emergency room, they presented with rhinorrhea and/or otorrhea. Between 2-5 ml samples of rhinorrhea or otorrhea fluids were collected and sent to the hospital laboratory for analysis. Their chloride, sugar, and beta transferrin levels were measured. Test results were ready after about 90 minutes using conventional laboratory methods.

At the same time that the collected samples were sent to the laboratory, a few drops of each sample were contacted with the presently disclosed device and the results were obtained in less than 100 seconds for all samples at the patient's bedside. The time range for obtaining the results (to show whether CSF is present or not in the sample) using the presently disclosed device was from about 3 seconds to about 30 seconds. The time for a readout from all 20 samples was typically about 10 seconds. Under no circumstance, did it take longer than 50 seconds for the presently disclosed device to give a result (positive or negative for presence of CSF in the sample).

In one example, the red light comes on the presently disclosed device (to indicate CSF leakage) only if the glucose level in the sample being tested is 40-80 mg/dl and the chloride level in the sample is in the range of 116-128 mmol/L. In one example, the red light comes on the presently disclosed device (to indicate CSF leakage) only if the glucose level in the sample being tested is 40 mg/dl or above and the chloride level in the sample is 116 mmol/L or above. In one embodiment, if either the glucose in the sample is lower than 40 mg/dl or the chloride level in the sample is lower than 116 mmol/L, the green light indicates there is no CSF leakage.

In one study, 20 subjects with Cerebrospinal fluid leakage Symptoms underwent a laboratory test as a golden standard to diagnosis of CSF leakage. The sensitivity and specificity of the presently disclosed portable device as a screening tool was also assessed in the same subjects compared with the standard laboratory test that takes much longer. Distribution of Diagnosed (Positive/negative) cases in study subjects was determined by using diagnostic methods.

The laboratory evidence of CSF leakage in 18 subjects was confirmed (out of the 20 subjects with cerebrospinal fluid leakage symptoms), as per standard laboratory tests. Therefore, the prevalence of the event was 90% in the study subjects. Of these, 16 were also shown to be positive using the presently disclosed portable device. The diagnostic sensitivity and specificity of the presently taught portable device were 89% and 100%, respectively. Sensitivity and specificity are statistical measures of the performance of a binary classification test, also known in statistics as classification function: Sensitivity (also called the true positive rate, or the recall in some fields) measures the proportion of positives that are correctly identified as such (e.g., the percentage of sick people who are correctly identified as having the condition). Specificity (also called the true negative rate) measures the proportion of negatives that are correctly identified as such (e.g., the percentage of healthy people who are correctly identified as not having the condition). Thus, sensitivity quantifies the avoiding of false negatives, as specificity does for false positives.

The comparison of the conventional laboratory test results (that take 1-2 hours to perform) compared to the results of the presently disclosed invention (that takes seconds to perform) showed that the two assays, with respect to positive and negative results, showed 90% the same result. Since this simple measure does not take into account the agreement occurring by chance. Therefore, Kappa statistics (Cohen's kappa coefficient) was used to measure agreement. In this instance, the kappa was 0.615. This value was statistically significant (p value=0.003). A kappa of 0.615 is in the "moderate" agreement range between our two diagnostic tools. The estimated kappa itself could be due to chance, therefore, the P value in this case tests whether the estimated kappa is not due to chance.

The presently disclosed device, which provides very fast results for the physician in an emergency head trauma situation, is a highly desirable device for any hospital and similar emergency room or situation setting. The device provided an accuracy and efficiency of 80% at patient bedside and since results were immediately obtained, it provides for an immense improvement and desired solution to an existing problem in the art. In one embodiment, the test results can be obtained within 180 seconds of the sample being contacted with the portable hand-held device. That is, in this example, within 180 seconds, the presently disclosed device enables the operator to know if there is leakage of cerebrospinal fluid occurring in the patient. Since these situations are typically high medical emergencies, speed is of the essence and this quick and very accurate hand held device can be used at the bedside in emergency rooms and the use of which can effectively save lives. In one example, the test results can be obtained within 60 seconds of the sample being contacted with the portable hand-held device. In one example, the test results can be obtained within 40 seconds of the sample being contacted with the portable hand-held device. In one example, the test results can be obtained within 20 seconds of the sample being contacted with the portable hand-held device.

One aspect of the present disclosure is directed to a method for rapidly detecting cerebrospinal fluid (CSF) in a sample. The method comprises providing a portable hand-held device for detecting CSF in the sample, wherein the device comprises a sample pad operatively connected to an analyzer, a display unit and an indicator, wherein the analyzer comprises sensors capable of detecting glucose and chloride in the sample. The method further comprises taking a sample secretion from an ear or nose; and placing on the sample pad of the device, a predefined quantity of the sample secretion taken from the ear or nose. The method further comprises observing a readily discernible change in the indicator unit, indicating the presence or absence of glucose and chloride. Moreover, the method further comprises reading an output from the display unit of the device, wherein the output is obtained under one minute from placing the sample secretion on the sample pad of the device, such that the presence of both glucose and chloride are indicative of the presence of cerebrospinal fluid in the sample. In one example, the display unit displays the concentration of the glucose and chloride present in the sample. CSF leakage is detected, in one example, if the glucose level in the sample is between 40-80 mg/dl and the chloride level in the sample is between 116-128 mmol/L.

One aspect of the present disclosure is directed to a method for rapidly detecting cerebrospinal fluid (CSF) in a sample. The method comprises providing a portable hand-held device for detecting CSF in the sample, with the device itself comprising a sample pad operatively connected to an analyzer, a display unit and an indicator. The analyzer comprises one or more sensors capable of detecting at least one analyte in the sample, and the at least one analyte is selected from a group consisting of glucose, chloride, and beta-transferrin. The method for rapidly detecting CSF in a sample further comprises taking a sample secretion from an ear or nose, and placing on the sample pad of the device a predefined quantity of the sample secretion taken from the ear or nose. The method further includes observing a readily discernible change in the indicator unit, indicating the presence or absence of one or more of analytes selected from the group consisting of glucose, chloride, and beta-transferrin. The method also includes reading an output from the display unit of the device, wherein the output displays the concentration of one or more of the analytes present in the fluid sample taken from the ear or nose. This output is obtained under three minutes from placing the sample secretion on the sample pad of the device. Furthermore, the method indicates the presence of one or more of glucose, chloride, or beta-transferrin at a particular concentration and this is indicative of the presence of cerebrospinal fluid in the sample. In one embodiment, the analyte is glucose or chloride.

Another aspect of the present disclosure is directed to a method for rapidly detecting cerebrospinal fluid leakage in a patient. The method comprises providing a portable hand-held device for detecting the presence or absence of CSF in a fluid sample from the patient, where the portable hand-held device comprises a sample pad operatively connected to an analyzer and a display unit. The method further comprises collecting a sample of a secretion from the nose or the ear of the patient; and placing on the sample pad of the device, a predefined quantity of the sample. The analyzer is capable of detecting the presence and concentration in the sample of one or more analytes selected from a group consisting of glucose, chloride, and beta-transferrin. The method further comprises detecting the presence or absence of the one or more analytes in under three minutes and based on this, observing a readily discernible change in an indicator on the display unit, the result of which indicates the presence or absence of cerebrospinal fluid in the sample and by extension provides for the rapid detection of cerebrospinal fluid leakage in a patient. In one embodiment, the analyte is glucose or chloride.

Another aspect of the present disclosure is directed to a portable hand-held device for detecting cerebrospinal fluid in a fluid sample from the ear or nose of a patient. The device comprises a sample pad comprising one or more sensors capable of detecting at least one analyte in a fluid sample taken from the ear or nose of a patient. The analyte is selected from a group consisting of glucose, chloride, and beta-transferrin. The device further comprises an analyzer operatively connected to the sample pad, wherein the analyzer quantitative analyses the presence or absence of analytes selected from the group consisting of glucose, chloride, and beta-transferrin. The device further comprises a display unit operably connected to the analyzer, for displaying an output of the analysis, such that the display unit comprises an indicator for indicating the presence or the absence of cerebrospinal fluid in a fluid sample. In one embodiment, the analyte is glucose or chloride.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method.

Many modifications and other embodiments of the invention will come to mind to one skilled in the art to which this invention pertains having the benefit of the teachings presented in the foregoing descriptions. Although specific terms may be employed herein, they are used only in generic and descriptive sense and not for purposes of limitation. Accordingly, the present invention is not limited to the specific embodiments illustrated herein.

What is claimed is:

1. A portable hand-held device for detecting cerebrospinal fluid in a fluid sample from the ear or nose of a patient, comprising:
    a sample pad comprising one or more sensors capable of detecting glucose, chloride and beta-transferrin as analytes in a fluid sample taken from the ear or nose of a patient;
    an analyzer operatively connected to the sample pad, wherein the analyzer quantitatively analyses the presence or absence of glucose, chloride and beta-transferrin as analytes; and
    a display unit operably connected to the analyzer, for displaying an output of the analysis, wherein the display unit further comprises an indicator for indicating the presence or the absence of cerebrospinal fluid in said fluid sample based on quantitative output from the analyzer related to the presence or absence of glucose, chloride and beta-transferrin.

2. The device of claim 1, further comprises a serial communication interface operatively connected to the analyzer for connecting to a computing device.

3. The device of claim 1, wherein the device is no larger than 30 cm length, 15 cm width and 7 cm height, and wherein the indicator comprises a red light for indicating cerebrospinal fluid leakage and a green light for indicating no cerebrospinal fluid leakage.

4. The device of claim 1, wherein the analytes are glucose and chloride.

5. The device of claim 1, wherein the sample pad further comprises a sample port for receiving the sample fluid.

6. The device of claim 1, wherein the one or more sensors comprise a chemical sensor or an electrical sensor or both.

7. The device of claim 1, wherein the display unit further displays a standard concentration range of the one or more analytes from the group consisting of glucose, chloride, and beta-transferrin for adults and children.

8. A method for rapidly detecting cerebrospinal fluid leakage in a patient, comprising:
    i) providing a portable hand-held device for detecting the presence or absence of CSF in a fluid sample from the patient, wherein the portable hand-held device comprises a sample pad operatively connected to an analyzer and a display unit;
    ii) collecting a sample of a secretion from the nose or the ear of the patient;
    iii) placing on the sample pad of the device, a predefined quantity of the sample, wherein the analyzer is capable of detecting the presence and concentration in the sample of glucose, chloride, and beta-transferrin as analytes;
    iv) detecting the presence or absence of the analytes in under three minutes; and
    v) observing a readily discernible change in an indicator on the display unit, which indicates the presence or absence of cerebrospinal fluid in the sample based on quantitative output from the analyzer related to the presence or absence of glucose, chloride and beta-transferrin and by extension provides for the rapid detection of cerebrospinal fluid leakage in the patient.

9. The method of claim 8, wherein the analytes are glucose and chloride.

10. The method of claim 8, wherein the device is a portable, hand held device and the indicator comprises a red light for indicating cerebrospinal fluid leakage and a green light for indicating no cerebrospinal fluid leakage.

11. The method of claim 8, wherein the sample pad further comprises a sample port for receiving said sample secretion.

12. The method of claim 8, wherein the analyzer is selected from a group consisting of a chemical sensor and an electrical sensor.

13. The method of claim 8, wherein the display unit further displays a standard concentration range of the analytes for adults and children.

14. The method of claim 8, wherein if the glucose concentration in the sample is 40 mg/dl or above and the chloride concentration in the sample is 116 mmol/L or above, CSF leakage is detected.

15. A method for rapidly detecting cerebrospinal fluid (CSF) in a sample, said method comprising:
    i) providing a portable hand-held device for detecting CSF in the sample, wherein the device comprises a sample pad operatively connected to an analyzer, a display unit and an indicator, wherein the analyzer comprises sensors capable of detecting glucose and chloride in the sample;

ii) taking a sample secretion from an ear or nose;
iii) placing on the sample pad of the device, a predefined quantity of the sample secretion taken from the ear or nose;
iv) observing a readily discernible change in the indicator, indicating the presence or absence of glucose and chloride in the sample secretion; and
v) reading an output from the display unit of the device, wherein the output is obtained in under one minute from placing the sample secretion on the sample pad of the device, and wherein the presence of both glucose and chloride are indicative of the presence of cerebrospinal fluid in the sample secretion.

16. The method of claim 15, wherein CSF leakage is detected if the glucose level in the sample is between 40-80 mg/dl and the chloride level in the sample is between 116-128 mmol/L.

17. The method of claim 15, wherein the indicator comprises a red light for indicating cerebrospinal fluid leakage and a green light for indicating no cerebrospinal fluid leakage.

18. The method of claim 15, wherein the sample pad further comprises a sample port for receiving the sample secretion.

19. The method of claim 15, wherein the sensors are selected from a group consisting of a chemical sensor and an electrical sensor.

20. The method of claim 15, wherein if the glucose level in the sample is 40 mg/dl or above and the chloride level in the sample is 116 mmol/L or above, CSF leakage is detected.

* * * * *